United States Patent
Park et al.

(10) Patent No.: US 10,076,308 B2
(45) Date of Patent: Sep. 18, 2018

(54) ULTRASONIC DIAGNOSIS APPARATUSES FOR GENERATING HARMONIC IMAGES AND METHODS OF GENERATING ULTRASONIC IMAGES INCLUDING HARMONIC IMAGES

(71) Applicant: Samsung Electronics Co., Ltd., Suwon-Si, Gyeonggi-Do (KR)

(72) Inventors: Sangha Park, Seoul (KR); Sungchan Kang, Hwaseong-si (KR); Seokwhan Chung, Hwaseong-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 810 days.

(21) Appl. No.: 14/595,518

(22) Filed: Jan. 13, 2015

(65) Prior Publication Data
US 2016/0051229 A1    Feb. 25, 2016

(30) Foreign Application Priority Data
Aug. 20, 2014  (KR) .................. 10-2014-0108456

(51) Int. Cl.
*A61B 8/00* (2006.01)
*G01S 7/52* (2006.01)
(Continued)

(52) U.S. Cl.
CPC ............... *A61B 8/463* (2013.01); *A61B 8/14* (2013.01); *A61B 8/5207* (2013.01); *A61B 8/54* (2013.01);
(Continued)

(58) Field of Classification Search
CPC .. A61B 8/54; A61B 8/14; A61B 8/463; G01S 7/52038; G01S 7/5202
See application file for complete search history.

(56) References Cited

U.S. PATENT DOCUMENTS 6,440,074 B1   8/2002  Averkiou
6,494,839 B1  12/2002  Averkiou
(Continued)

FOREIGN PATENT DOCUMENTS

| EP | 1126287 A2 | 8/2001 |
|---|---|---|
| EP | 1126287 A3 | 9/2004 |
| JP | 5242631 B2 | 7/2013 |

OTHER PUBLICATIONS

Che-Chou Shen et al., "Third Harmonic Transmit Phasing for Tissue Harmonic Generation," IEEE Transactions on Ultrasonics, Ferroelectrics and Frequency Control, IEEE, US, vol. 54, No. 7, Jul. 1, 2007 (Jul. 1, 2007), pp. 1370-1381, XP011188011, ISSN: 0885-3010, DOI: 10.1109/TUFFC.2007.397.
(Continued)

*Primary Examiner* — Joseph M Santos Rodriguez
(74) *Attorney, Agent, or Firm* — Harness, Dickey & Pierce, P.L.C.

(57) ABSTRACT

An ultrasonic diagnosis apparatus may comprise: a probe comprising a transducer configured to transmit a signal to an object and configured to receive an echo signal from the object; a controller configured to control the probe; and/or an image generation unit configured to generate an image of the object based on the echo signal. The controller may be further configured to drive the transducer such that the signal transmitted simultaneously comprises a fundamental frequency and at least one harmonic. A method of generating an ultrasonic image may comprise: transmitting a signal to an object by using a transducer; receiving an echo signal from the object by using the transducer; and/or generating an image of the object based on the echo signal. The transmitting of the signal to the object may comprise driving the transducer such that the signal transmitted simultaneously
(Continued)

comprises a fundamental frequency and at least one harmonic.

18 Claims, 8 Drawing Sheets

(51) Int. Cl.
    *G01S 15/89*     (2006.01)
    *A61B 8/14*     (2006.01)
    *A61B 8/08*     (2006.01)

(52) U.S. Cl.
    CPC ........ *G01S 7/5202* (2013.01); *G01S 7/52038* (2013.01); *G01S 15/8952* (2013.01); *G01S 15/8963* (2013.01)

(56) References Cited

U.S. PATENT DOCUMENTS

| | | |
|---|---|---|
| 6,532,819 B1 | 3/2003 | Chen et al. |
| 6,645,146 B1 | 11/2003 | Adams et al. |
| 2002/0128555 A1* | 9/2002 | Maxwell ............ A61B 8/54 600/447 |
| 2002/0147398 A1 | 10/2002 | Kawagishi et al. |
| 2004/0064043 A1 | 4/2004 | Rielly et al. |

OTHER PUBLICATIONS

European Patent Office Extended European Search Report dated Jan. 15, 2016, for Application No. 15158041.2-1812.

* cited by examiner

ULTRASONIC DIAGNOSIS APPARATUSES FOR GENERATING HARMONIC IMAGES AND METHODS OF GENERATING ULTRASONIC IMAGES INCLUDING HARMONIC IMAGES

CROSS-REFERENCE TO RELATED APPLICATION(S)

This application claims priority from Korean Patent Application No. 10-2014-0108456, filed on Aug. 20, 2014, in the Korean Intellectual Property Office (KIPO), the entire contents of which are incorporated herein by reference.

BACKGROUND

1. Field

Some example embodiments may relate generally to methods and apparatuses for ultrasonic diagnosis apparatuses for generating harmonic images. Some example embodiments may relate generally to methods of generating ultrasonic images including the harmonic images.

2. Description of Related Art

Ultrasonic diagnosis apparatuses may transmit ultrasonic signals to objects, such as humans or animals, may detect received echo signals reflected from the objects, may display sectional images of tissues of the objects, and may thereby provide information necessary for the diagnosis of the objects.

Probes of the ultrasonic diagnosis apparatuses may include ultrasonic transducers that convert electrical signals to ultrasonic signals, or vice versa. The ultrasonic transducers may include a plurality of 2-dimensionally arrayed ultrasonic cells. An ultrasonic cell may be a micro-machined ultrasonic transducer (MUT). For example, depending on conversion methods, the MUT may be a piezoelectric MUT (pMUT), a capacitive MUT (cMUT), or a magnetic MUT (mMUT).

SUMMARY

Some example embodiments may provide methods for ultrasonic diagnosis apparatuses for generating harmonic images.

Some example embodiments may provide apparatuses for ultrasonic diagnosis apparatuses for generating harmonic images.

Some example embodiments may provide methods of generating ultrasonic images including the harmonic images.

In some example embodiments, an ultrasonic diagnosis apparatus may comprise: an ultrasonic probe comprising an ultrasonic transducer configured to transmit an ultrasonic signal to an object and configured to receive an ultrasonic echo signal reflected from the object; a controller configured to control the ultrasonic probe; and/or an image generation unit configured to generate an ultrasonic image of the object based on the ultrasonic echo signal received by the ultrasonic probe. The controller may be further configured to drive the ultrasonic transducer such that the ultrasonic signal transmitted to the object simultaneously comprises a fundamental frequency and at least one harmonic of the fundamental frequency.

In some example embodiments, the controller may be further configured to drive the ultrasonic transducer such that the ultrasonic signal transmitted to the object simultaneously comprises the fundamental frequency and a first harmonic of the fundamental frequency.

In some example embodiments, the image generation unit may be further configured to generate a harmonic image by using a first harmonic of the ultrasonic echo signal received by the ultrasonic probe.

In some example embodiments, the first harmonic of the ultrasonic echo signal received by the ultrasonic probe may be a sum of a first harmonic component, generated by nonlinear response from the object with respect to the fundamental frequency of the ultrasonic signal transmitted to the object, and a first harmonic component, generated when the first harmonic of the ultrasonic signal transmitted to the object is reflected by linear response from the object.

In some example embodiments, the image generation unit may be further configured to generate a B-mode image by using a fundamental frequency of the ultrasonic echo signal received from the ultrasonic probe.

In some example embodiments, the apparatus may further comprise: a display unit configured to display at least one of the harmonic image and the B-mode image selected by the controller.

In some example embodiments, the controller may be further configured to drive the ultrasonic transducer such that the ultrasonic signal transmitted to the object simultaneously comprises the fundamental frequency and a second harmonic of the fundamental frequency.

In some example embodiments, the image generation unit may be further configured to generate a harmonic image by using a second harmonic of the ultrasonic echo signal received by the ultrasonic probe.

In some example embodiments, the controller may be further configured to drive the ultrasonic transducer such that the ultrasonic signal transmitted to the object simultaneously comprises the fundamental frequency, a first harmonic of the fundamental frequency, and a second harmonic of the fundamental frequency.

In some example embodiments, the image generation unit may be further configured to generate a B-mode image, by using a fundamental frequency of the ultrasonic echo signal received from the ultrasonic probe, or to generate a harmonic image, by using at least one selected from a first harmonic and a second harmonic of the ultrasonic echo signal received from the ultrasonic probe.

In some example embodiments, the controller may be further configured to drive the ultrasonic transducer such that the ultrasonic signal transmitted to the object simultaneously comprises the fundamental frequency and at least one selected from a first harmonic and a second harmonic of the fundamental frequency, depending on which is selected by a user.

In some example embodiments, a method of generating an ultrasonic image may comprise: transmitting an ultrasonic signal to an object by using an ultrasonic transducer; receiving an ultrasonic echo signal reflected from the object by using the ultrasonic transducer; and/or generating an ultrasonic image of the object based on the ultrasonic echo signal. The transmitting of the ultrasonic signal to the object may comprise driving the ultrasonic transducer such that the ultrasonic signal transmitted to the object simultaneously comprises a fundamental frequency and at least one harmonic of the fundamental frequency.

In some example embodiments, the ultrasonic signal transmitted to the object may simultaneously comprise the fundamental frequency and a first harmonic of the fundamental frequency.

In some example embodiments, the generating of the ultrasonic image may comprise generating a harmonic image by using a first harmonic of the ultrasonic echo signal.

In some example embodiments, the first harmonic of the ultrasonic echo signal may be a sum of a first harmonic component, generated by nonlinear response from the object with respect to the fundamental frequency of the ultrasonic signal transmitted to the object, and a first harmonic component, generated when the first harmonic of the ultrasonic signal transmitted to the object is reflected by linear response from the object.

In some example embodiments, the generating of the ultrasonic image may further comprise generating a B-mode image by using a fundamental frequency of the ultrasonic echo signal.

In some example embodiments, the method may further comprise: displaying at least one selected from the harmonic image and the B-mode image, depending on which is selected by a user.

In some example embodiments, the ultrasonic signal transmitted to the object may simultaneously comprise the fundamental frequency and a second harmonic of the fundamental frequency.

In some example embodiments, the ultrasonic signal transmitted to the object may simultaneously comprise the fundamental frequency, a first harmonic of the fundamental frequency, and a second harmonic of the fundamental frequency.

In some example embodiments, the transmitting of the ultrasonic signal to the object may comprise: selecting at least one from the at least one harmonic of the fundamental frequency; generating the ultrasonic signal comprising the fundamental frequency and the selected at least one harmonic; and/or transmitting the generated ultrasonic signal to the object.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
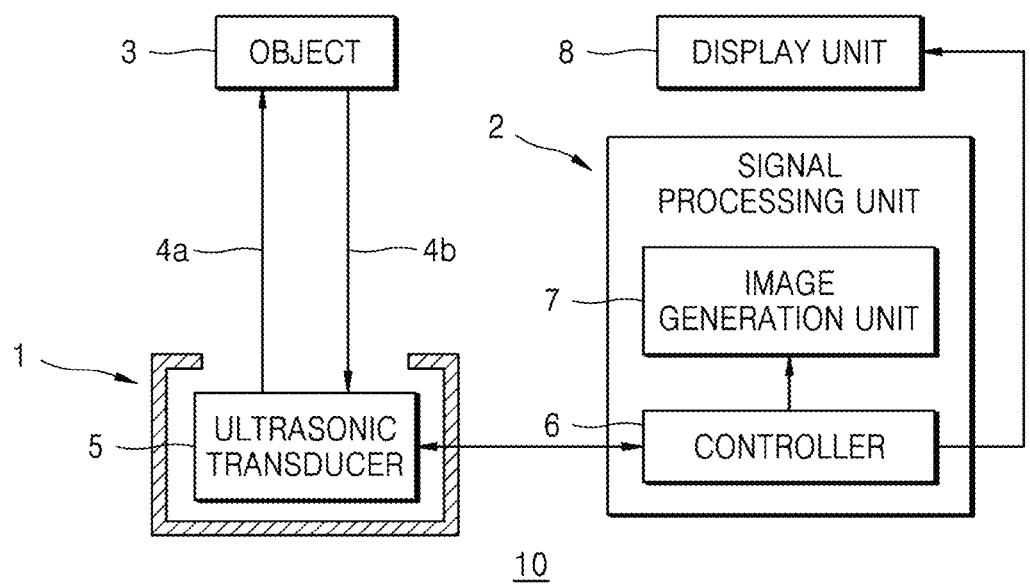
FIG. 1 is a schematic block diagram of a structure of an ultrasonic diagnosis apparatus according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

FIG. 1 is a schematic block diagram of a structure of an ultrasonic diagnosis apparatus 10 according to some example embodiments. Referring to FIG. 1, the ultrasonic diagnosis apparatus 10 may include an ultrasonic probe 1 and a signal processing unit 2. The ultrasonic probe 1 may include an ultrasonic transducer 5 that transmits an ultrasonic signal 4*a* to an object 3 (for example, a human body) and receives an ultrasonic echo signal 4*b* reflected from the object 3. Also, the ultrasonic probe 1 may further include a housing 9 that accommodates the ultrasonic transducer 5.

The signal processing unit 2 may control the ultrasonic probe 1 and generate an image of the object 3 based on the ultrasonic echo signal 4*b* that is detected by the ultrasonic probe 1 and includes information regarding the object 3. To do so, the signal processing unit 2 may include a controller 6 and an image generation unit 7. The controller 6 controls the ultrasonic transducer 5 such that the ultrasonic transducer 5 transmits the ultrasonic signal 4*a* and receives the ultrasonic echo signal 4*b*. For example, the controller 6 may determine a location where ultrasonic wave is to be transmitted and an intensity of the transmitted ultrasonic wave, and control the ultrasonic transducer 5 according to the determination result.

Also, the controller 6 may apply driving signals to the ultrasonic transducer 5 such that the ultrasonic transducer 5 may generate ultrasound signals having certain frequencies. Various ultrasonic signals may be generated in the ultrasonic transducer 5 according to the driving signals applied to the ultrasonic transducer 5 by the controller 6. According to the control of the controller 6, the ultrasonic transducer 5 may generate sine wave or pulse wave ultrasonic signals having certain frequencies and transmit the signals to the object 3. It will be understood by one of ordinary skill in the art that the controller 6 may also control general operations of the ultrasonic probe 1 that have not been described in detail.

The image generation unit 7 may generate ultrasonic images of the object 3 by using the ultrasonic echo signal 4*b* received from the ultrasonic probe 1. For example, according to the control of the controller 6, the image generation unit 7 may generate B-mode images by using a fundamental frequency of the ultrasonic echo signal 4*b* or harmonic images by using harmonics of the fundamental frequency $f_1$. Although not illustrated, the controller 6 may include an input device for receiving a command input from a user. Therefore, the user may select a B-mode image or a harmonic image by using the input device. Since general processes of generating the ultrasonic images are well-known to one of ordinary skill in the art, the detailed description thereof will be omitted.

The ultrasonic images may be displayed on a display unit 8. For example, the display unit 8 may display B-mode images or harmonic images. In particular, if the user selects a B-mode image by using the input device, the controller 6 may generate a B-mode image by using the image generation unit 7 and display the generated image on the display unit 8. Alternatively, if the user selects a harmonic image by using the input device, the controller 6 may generate a harmonic image by using the image generation unit 7 and display the generated image on the display unit 8. Alternatively, depending on which is selected by the user, a B-mode image and a harmonic image may both be generated and displayed together on the display unit 8.

The signal processing unit 2 may be, for example, a processor including an array of a plurality of logic gates, or a combination of a universal microprocessor and a memory in which a program executable in the microprocessor is stored. It will be understood by one of ordinary skill in the art to which the present application pertains that the signal processing unit 2 may be implemented by other appropriate types of hardware.

In general, the resolutions of the ultrasonic images generated in the image generation unit 7 may be proportional to a frequency of the ultrasonic signal 4*a* that is used. Also, the frequency of the ultrasonic signal 4*a* may be determined according to a depth of tissues to be observed. That is, if tissues in deep parts of the object 3 are to be observed, a relatively low frequency (for example, 5 megahertz (MHz) or less) is used, and if tissues in shallow parts of the object 3 are to be observed, a relatively high frequency may be used. Since a relatively low frequency used when the tissues in the deep parts of the object 3 are observed, the resolutions of the ultrasonic images may be decreased.

Harmonic imaging is proposed to observe the tissues in the deep parts of the object 3 in higher resolution images. The harmonic imaging method uses harmonics that are generated by a nonlinear response from tissues of the object 3. Due to the nonlinearity of the tissues of the object 3, the harmonics, which are integer multiples of the frequency of the transmitted ultrasonic signal, are generated while the ultrasonic signal 4*a* proceeds through the tissues of the object 3. Then, such harmonics may be detected to generate high resolution images. For example, when the ultrasonic signal 4*a* having a frequency of 1 MHz is transmitted to the object 3, the ultrasonic echo signal 4*b* reflected from the object 3 may have frequencies of 1 MHz, 2 MHz, 3 MHz, etc. In the ultrasonic echo signal 4*b*, a frequency of 1 MHz is generated by a linear response from the object 3, and frequencies of 2 MHz, 3 MHz, etc. are generated by nonlinear response from the object 3. Images generated by using the frequency of 1 MHz of the ultrasonic echo signal 4*b* are referred to as B-mode images, and images generated by using the frequencies of 2 MHz, 3 MHz, etc. are referred to as harmonic images.

Since the harmonic images are generated by using higher frequencies, the harmonic images may have higher resolutions, less speckle noise, and sharper edges than the B-mode images. Therefore, the harmonic imaging method may be used when a relatively low frequency needs to be used to observe organs in deep parts of a body. However, since harmonic signals generated by the nonlinear response are not strong, the quality of the harmonic images may be sensitive to an output of the ultrasonic transducer 5 or the nonlinearity of the tissues, and it may be difficult to receive the harmonic signals. Also, if the intensity of the ultrasonic signal 4a transmitted to the object 3 is increased to increase the intensities of the harmonic signals, the tissues of the object 3 may be damaged. Thus, the intensity of the ultrasonic signal 4a transmitted to the object 3 is limited.

According to some example embodiments, in order to increase the intensities of harmonics of the ultrasonic echo signal 4b received from the object 3, the ultrasonic transducer 5 may be driven such that the ultrasonic signal 4a transmitted to the object 3 by the ultrasonic transducer 5 simultaneously has a fundamental frequency and at least one harmonic of the fundamental frequency. The operations of the ultrasonic transducer 5 may be controlled by the controller 6.

Figure 2:
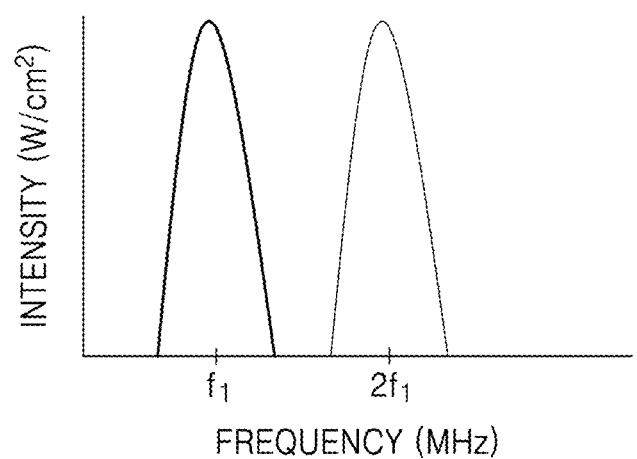
FIG. 2 is a graph of an example of frequencies of an ultrasonic signal generated in an ultrasonic transducer.
Figure 3:
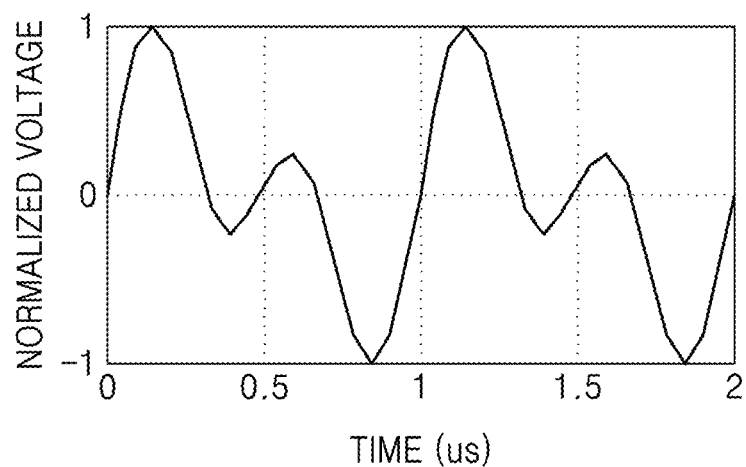
FIG. 3 is a graph of an example of driving signals applied to an ultrasonic transducer.

For example, FIG. 2 is a graph of an example of frequencies of the ultrasonic signal 4a generated in the ultrasonic transducer 5. Referring to FIG. 2, the ultrasonic signal 4a generated in the ultrasonic transducer 5 may have a fundamental frequency $f_1$ and a first harmonic $2f_1$ of the fundamental frequency $f_1$. The controller 6 may apply a desired driving signal (that may or may not be predetermined) to the ultrasonic transducer 5 so that the ultrasonic transducer 5 may generate the ultrasonic signal 4a shown in FIG. 2. For example, FIG. 3 is a graph of an example of driving signals applied to the ultrasonic transducer 5 by the controller 6. Apart from the driving signals shown in FIG. 3, for example, a plurality of pulses having the same intensity may be applied to the ultrasonic transducer 5 at certain time intervals.

Figure 4A:
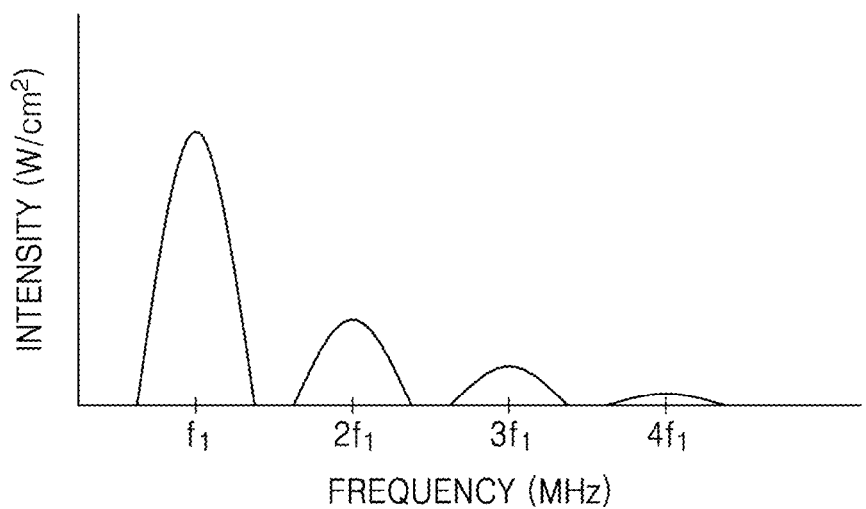
FIG. 4A is a graph of an example of frequencies of an ultrasonic echo signal received from an object when an ultrasonic signal that only has a fundamental frequency is transmitted to the object.
Figure 4B:
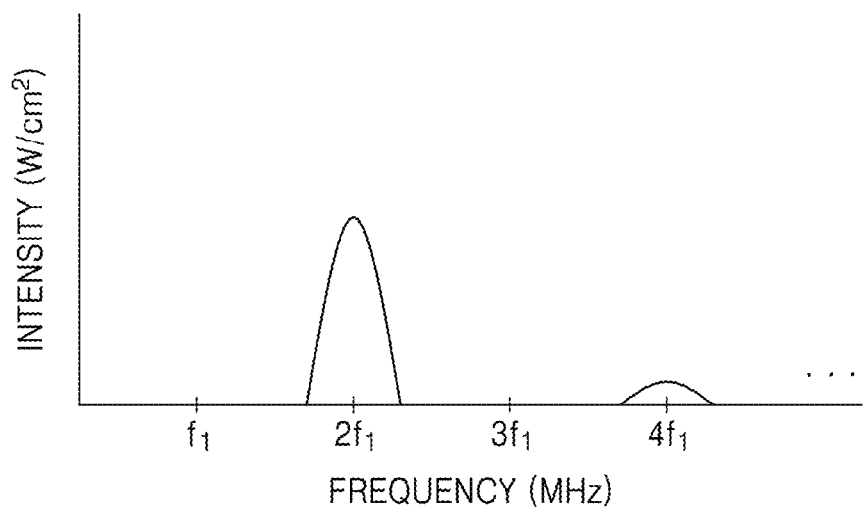
FIG. 4B is a graph of an example of frequencies of an ultrasonic echo signal received from an object when an ultrasonic signal that only has a first harmonic is transmitted to the object.
Figure 4C:
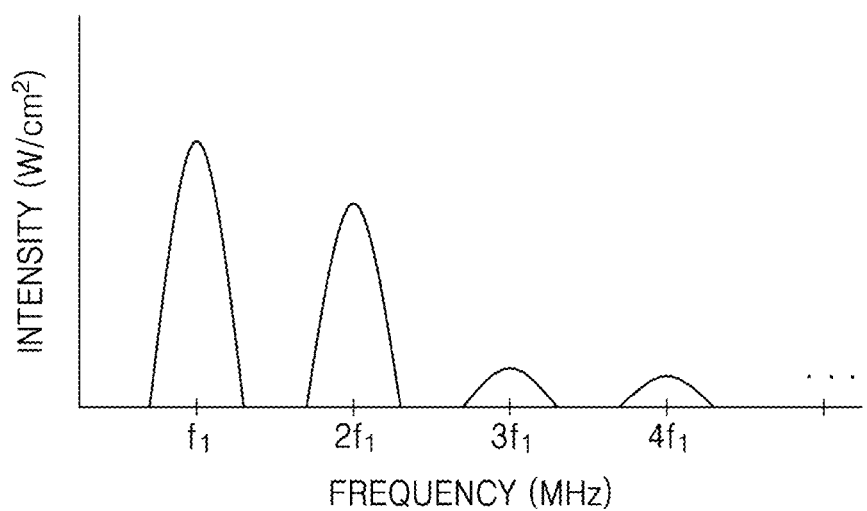
FIG. 4C is a graph of an example of frequencies of an ultrasonic echo signal received from an object when an ultrasonic signal that simultaneously has a fundamental frequency and a first harmonic is transmitted to the object.

As shown in FIG. 2, since the ultrasonic signal 4a that simultaneously has the fundamental frequency $f_1$ and the first harmonic $2f_1$ is transmitted to the object 3, an intensity of the first harmonic $2f_1$ of the ultrasonic echo signal 4b received from the object 3 may be increased. FIGS. 4A to 4C are provided to describe principles related thereto. FIG. 4A is a graph of an example of frequencies of the ultrasonic echo signal 4b when the ultrasonic signal 4a that only has the fundamental frequency $f_1$ is transmitted to the object 3. FIG. 4B is a graph of an example of frequencies of the ultrasonic echo signal 4b received from the object 3 when the ultrasonic signal 4a that only has the first harmonic $2f_1$ is transmitted to the object 3. FIG. 4C is a graph of an example of frequencies of the ultrasonic echo signal 4b received from the object 3 when the ultrasonic signal 4a that simultaneously has the fundamental frequency $f_1$ and the first harmonic $2f_1$ is transmitted to the object 3.

First, referring to FIG. 4A, when the ultrasonic signal 4a that only has the fundamental frequency $f_1$ is transmitted to the object 3, the ultrasonic echo signal 4b received from the object 3 may have the fundamental frequency $f_1$ and a plurality of harmonics ($2f_1$, $3f_1$, $4f_1$, ... ). The fundamental frequency $f_1$ of the ultrasonic echo signal 4b is generated when the fundamental frequency $f_1$ of the ultrasonic signal 4a is reflected from the object 3 due to a linear response from the object 3. Also, the harmonics ($2f_1$, $3f_1$, $4f_1$, ... ) of the ultrasonic echo signal 4b are generated by a nonlinear response from the object 3. As shown in FIG. 4A, the intensities of the harmonics ($2f_1$, $3f_1$, $4f_1$, ... ) are much smaller than the intensity of the fundamental frequency $f_1$, and decrease more and more according to the order of the harmonics ($2f_1$, $3f_1$, $4f_1$, ... ). As described above, since the intensities of the harmonics ($2f_1$, $3f_1$, $4f_1$, ... ) of the ultrasonic echo signal 4b are small, the quality of the harmonic image may be decreased.

Also, referring to FIG. 4B, when the ultrasonic signal 4a that only has the first harmonic $2f_1$ is transmitted to the object 3, the ultrasonic echo signal 4b received from the object 3 may have the first harmonic $2f_1$ and a third harmonic $4f_1$. Although not shown in FIG. 4B, along with the third harmonic $4f_1$, the ultrasonic echo signal 4b may also have a fifth harmonic $6f_1$ and a seventh harmonic $8f_1$. The first harmonic $2f_1$ of the ultrasonic echo signal 4b is generated when the first harmonic $2f_1$ of the ultrasonic signal 4a is reflected from the object 3 by a linear response from the object 3. The third harmonic $4f_1$ of the ultrasonic echo signal 4b is generated by a nonlinear response from the object 3.

According to some example embodiments, as in the example shown in FIG. 2, when the ultrasonic signal 4a that simultaneously has the fundamental frequency $f_1$ and the first harmonic $2f_1$ is transmitted to the object 3, the frequency of the ultrasonic echo signal 4b received from the object 3 may be the same as a sum of the graphs shown in FIGS. 4A and 4B. For example, referring to FIG. 4C, the first harmonic $2f_1$ shown in FIG. 4A and the first harmonic $2f_1$ shown in FIG. 4B are added and, thus, the intensity of the first harmonic $2f_1$ is greatly increased in the ultrasonic echo signal 4b. That is, when the ultrasonic signal 4a that simultaneously has the fundamental frequency $f_1$ and the first harmonic $2f_1$ is transmitted to the object 3, the first harmonic $2f_1$ is greatly increased in the ultrasonic echo signal 4b received from the object 3. In this case, the first harmonic $2f_1$ of the ultrasonic echo signal 4b is obtained by combining a component generated by nonlinear response to the fundamental frequency $f_1$ of the ultrasonic signal 4a and a component generated when the first harmonic $2f_1$ of the ultrasonic signal 4a is reflected from the object 3. According to some example embodiments, since the intensity of the first harmonic $2f_1$ of the ultrasonic echo signal is increased, harmonic images may be easily generated and the quality of the harmonic images may be improved.

Figure 5:
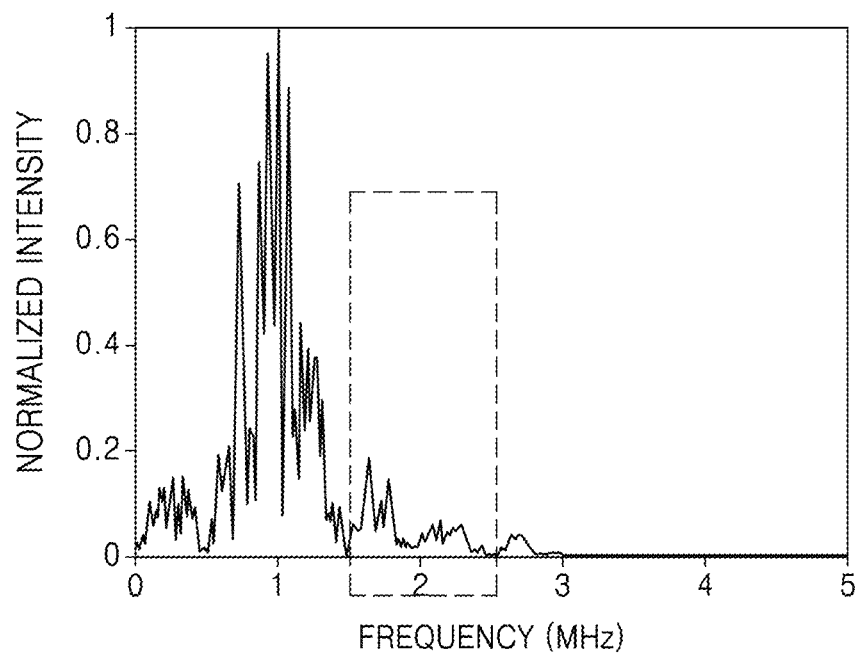
FIG. 5 is a graph of a simulation result of an ultrasonic echo signal received from an object when an ultrasonic signal that only has a fundamental frequency is transmitted to the object.
Figure 6:
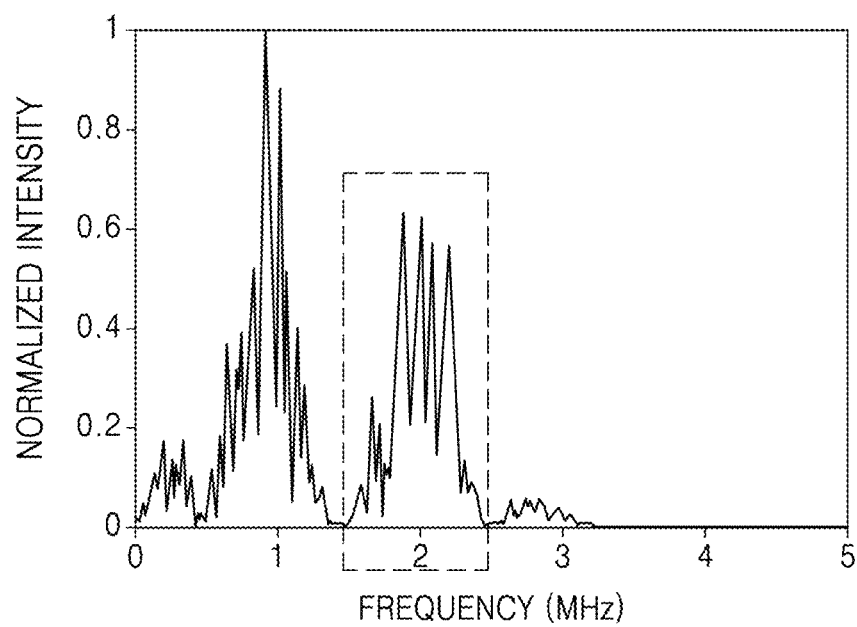
FIG. 6 is a graph of a simulation result of an ultrasonic echo signal received from an object when an ultrasonic signal that simultaneously has a fundamental frequency and a first harmonic is transmitted to the object.

FIG. 5 is a graph of a simulation result of the ultrasonic echo signal 4b received from the object 3 when the ultrasonic signal 4a that only has the fundamental frequency $f_1$ is transmitted to the object 3. FIG. 6 is a graph of a simulation result of the ultrasonic echo signal 4b received from the object 3 when the ultrasonic signal 4a that simultaneously has the fundamental frequency $f_1$ and the first harmonic $2f_1$ is transmitted to the object 3. Simulation parameters were set as below. That is, it is assumed that a width of the ultrasonic transducer 5 is 5 millimeters (mm), the number of ultrasonic elements of the ultrasonic transducer 5 is 20, a pitch of the ultrasonic elements is 0.25 mm, a length of the ultrasonic elements is 12 mm, a focal distance of the ultrasonic transducer 5 is 30 mm, a steering angle of the ultrasonic probe 1 ranges from about −30° to about +30°, an observation range is 50×30×12.5 mm, a medium characteristic of the object 3 is tissues, and a ball having a radius of 8 mm, highly scattering characteristic, and a sonic speed of about 1,450 m/s to about 1,700 m/s is provided inside the tissues of the object 3. The intensity of the first harmonic $2f_1$ is marked with a dashed box in FIGS. 5 and 6. The intensity of the first harmonic $2f_1$ in FIG. 6 is much greater than the intensity of the first harmonic $2f_1$ in FIG. 5. Therefore, when the ultrasonic signal 4a that simultaneously has the fundamental frequency $f_1$ and the first harmonic $2f_1$ is transmitted to the object 3, the first harmonic $2f_1$ is increased in the ultrasonic echo signal 4b received from the object 3.

Figure 7:
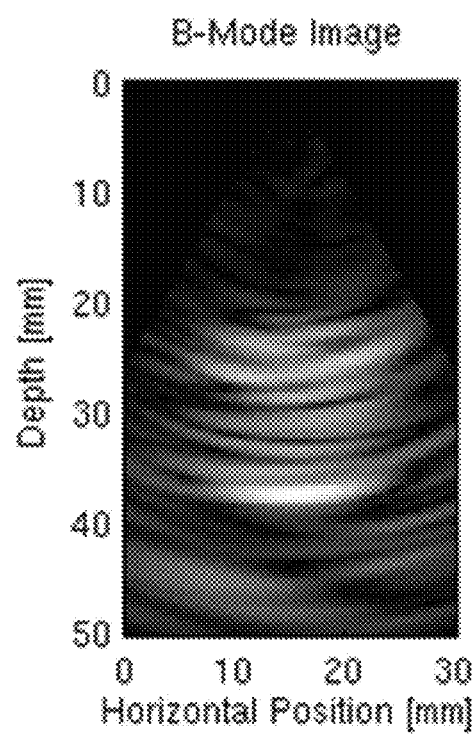
FIG. 7 is an exemplary simulation result of a B-mode image obtained by transmitting an ultrasonic signal that only has a fundamental frequency to an object.
Figure 8:
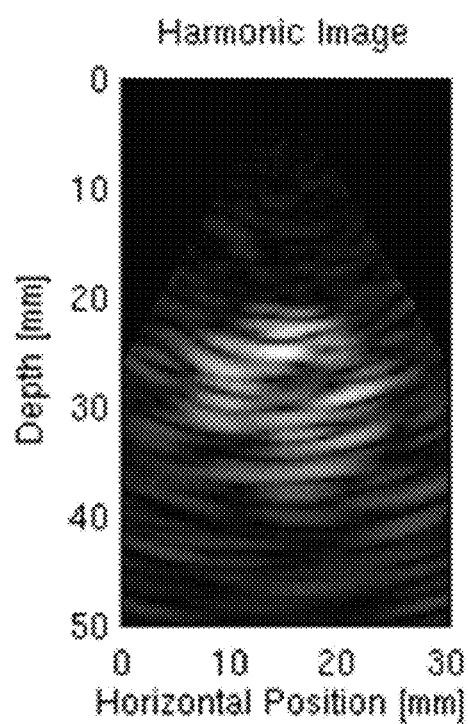
FIG. 8 is an exemplary simulation result of a harmonic image obtained by transmitting an ultrasonic signal that only has a fundamental frequency to an object.
Figure 9:
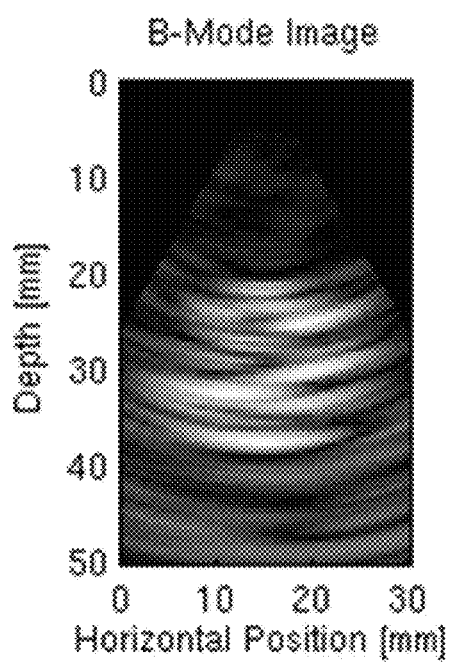
FIG. 9 is an exemplary simulation result of a B-mode image obtained by transmitting an ultrasonic signal that simultaneously has a fundamental frequency and a first harmonic to an object.
Figure 10:
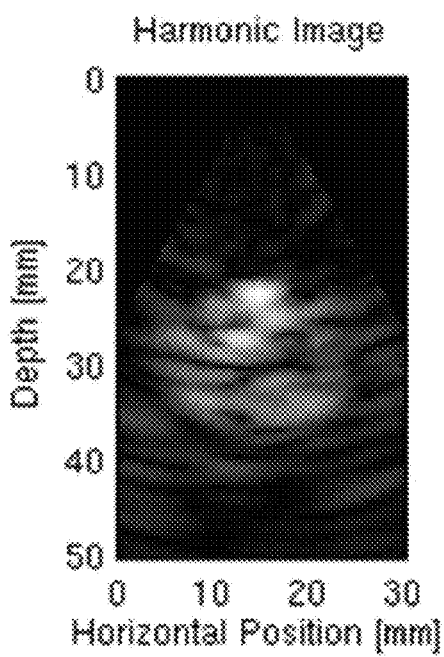
FIG. 10 is an exemplary simulation result of a harmonic image obtained by transmitting an ultrasonic signal that simultaneously has a fundamental frequency and a first harmonic to an object.

FIG. 7 is an exemplary simulation result of a B-mode image obtained by transmitting the ultrasonic signal 4a that only has the fundamental frequency $f_1$ to the object 3. FIG. 8 is an exemplary simulation result of a harmonic image obtained by transmitting the ultrasonic signal 4a that only has the fundamental frequency $f_1$ to the object 3. FIG. 9 is an exemplary simulation result of a B-mode image obtained by transmitting the ultrasonic signal 4a that simultaneously has the fundamental frequency $f_1$ and the first harmonic $2f_1$ to the object 3. FIG. 10 is an exemplary simulation result of a harmonic image obtained by transmitting the ultrasonic signal 4a that simultaneously has the fundamental frequency $f_1$ and the first harmonic $2f_1$ to the object 3. Simulations in FIGS. 7 to 10 have been conducted under the same conditions as in the simulations in FIGS. 5 and 6. Referring to FIGS. 7 to 10, the contour of the ball is observed more clearly (that is, in a spherical shape) in FIGS. 9 and 10. Therefore, when the ultrasonic signal 4a that simultaneously has the fundamental frequency $f_1$ and the first harmonic $2f_1$ is transmitted to the object 3, a high quality ultrasonic image may be obtained.

The example in which the ultrasonic signal 4a generated in the ultrasonic transducer 5 has the fundamental frequency $f_1$ and the first harmonic $2f_1$, and the harmonic image is generated by using the first harmonic $2f_1$ of the ultrasonic echo signal 4b reflected from the object 3, is described with reference to FIGS. 2 to 10. However, higher order harmonics may be used instead of the first harmonic $2f_1$.

Figure 11:
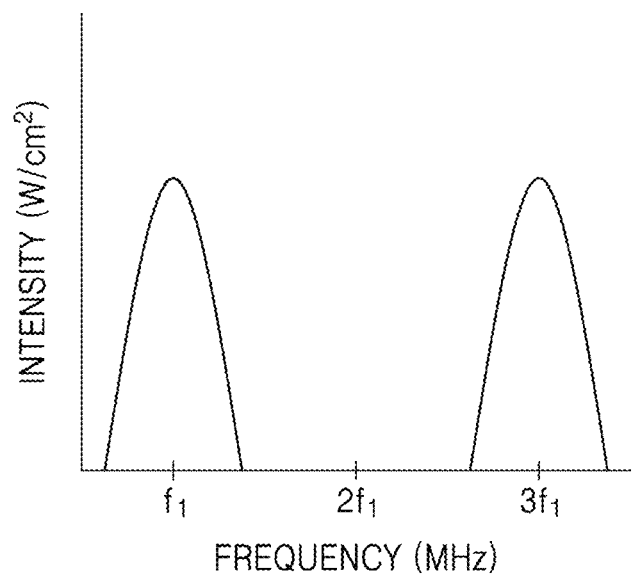
FIG. 11 is a graph of an example of an ultrasonic signal that simultaneously has a fundamental frequency and a second harmonic.
Figure 12:
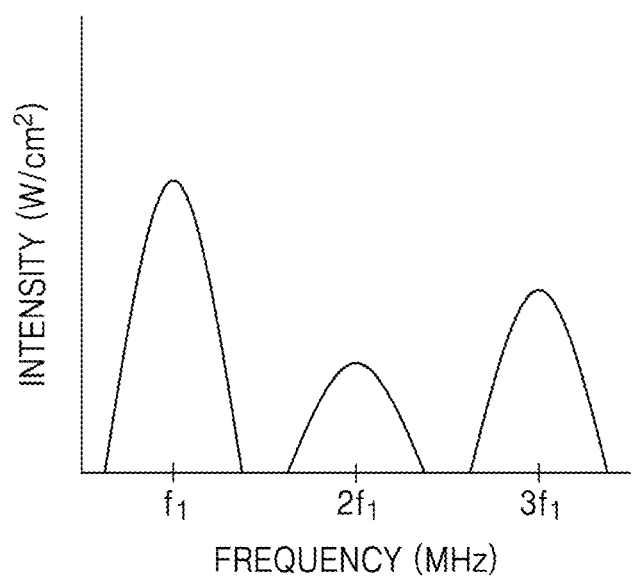
FIG. 12 is a graph of an example of frequencies of an ultrasonic echo signal received from an object when an ultrasonic signal that simultaneously has a fundamental frequency and a second harmonic is transmitted to the object.

For example, FIG. 11 is a graph of an example of the ultrasonic signal 4a that simultaneously has the fundamental frequency $f_1$ and a second harmonic $3f_1$. FIG. 12 is a graph of an example of frequencies of the ultrasonic echo signal 4b received from the object 3 when the ultrasonic signal 4a that simultaneously has the fundamental frequency $f_1$ and the second harmonic $3f_1$ is transmitted to the object 3. As described above, the second harmonic $3f_1$ of the ultrasonic echo signal 4b received from the object 3 is generated by combining a component generated by nonlinear response to the fundamental frequency $f_1$ of the ultrasonic signal 4a, and a component generated when the second harmonic $3f_1$ of the ultrasonic signal 4a is reflected by a linear response from the object. Therefore, as shown in FIG. 12, the second harmonic $3f_1$ of the ultrasonic echo signal 4b may be increased. According to the control of the controller 6, the image generation unit 7 may generate a B-mode image by using the fundamental frequency $f_1$ of the ultrasonic echo signal 4b or a harmonic image by using the second harmonic $3f_1$.

Figure 13:
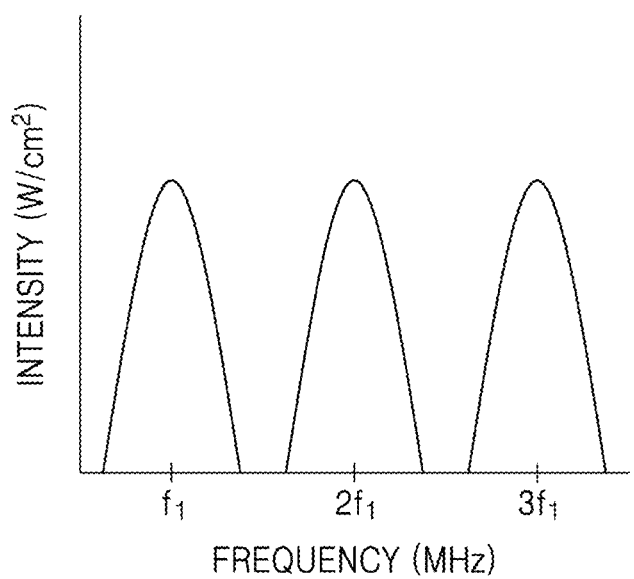
FIG. 13 is a graph of an example of an ultrasonic signal that simultaneously has a fundamental frequency, a first harmonic, and a second harmonic.

FIG. 13 is a graph of an example of the ultrasonic signal 4a that simultaneously has the fundamental frequency $f_1$, the first harmonic $2f_1$, and the second harmonic $3f_1$. As shown in FIG. 13, the ultrasonic signal 4a generated in the ultrasonic transducer 5 may simultaneously have the fundamental frequency $f_1$, the first harmonic $2f_1$, and the second harmonic $3f_1$. The controller 6 may apply a desired driving signal (that may or may not be predetermined) to the ultrasonic transducer 5 so that the ultrasonic transducer 5 may generate the ultrasonic signal 4a shown in FIG. 13. Then, the first and second harmonics $2f_1$ and $3f_1$ of the ultrasonic echo signal 4b received from the object 3 may be increased. Depending on which is selected by the user, the image generation unit 7 may generate a B-mode image by using the fundamental frequency $f_1$ of the ultrasonic echo signal 4b or a harmonic image by using at least one selected from the first harmonic $2f_1$ and the second harmonic $3f_1$. For example, the image generation unit 7 may use the first harmonic $2f_1$ to generate a first harmonic image or use the second harmonic $3f_1$ to generate a second harmonic image. Alternatively, the image generation unit 7 may generate both the first and second harmonic images.

The controller 6 may control the ultrasonic transducer 5 such that the ultrasonic signal 4a has at least one selected from the first harmonic $2f_1$, the second harmonic $3f_1$, and other higher order harmonics ($4f_1$, $5f_1$, ... ), depending on which is selected by the user. For example, if the user selects the first harmonic $2f_1$ by using the input device, the controller 6 may control the ultrasonic transducer 5 such that the ultrasonic signal 4a simultaneously has the fundamental frequency $f_1$ and the first harmonic $2f_1$. Alternatively, if the user selects the second harmonic $3f_1$ by using the input device, the controller 6 may control the ultrasonic transducer 5 such that the ultrasonic signal 4a simultaneously has the fundamental frequency $f_1$ and the second harmonic $3f_1$. Alternatively, if the user selects the first harmonic $2f_1$ and the second harmonic $3f_1$ by using the input device, the controller 6 may control the ultrasonic transducer 5 such that the ultrasonic signal 4a simultaneously has the fundamental frequency $f_1$, the first harmonic $2f_1$, and the second harmonic $3f_1$. Then, the ultrasonic transducer 5 may transmit the ultrasonic signal 4a that is generated to the object 3.

The controller 6 may store harmonics that are selected by the user in a memory device. Then, the controller 6 may receive the ultrasonic echo signal 4b reflected from the object 3, and then may transmit a command regarding which harmonic is used to generate an image to the image generation unit 7. For example, if the user selects the first harmonic $2f_1$ during a process of generating the ultrasonic signal 4a, the controller 6 may provide a screen on the display unit 8 so that the user may select from a B-mode image and a harmonic image generated by using the first harmonic $2f_1$. If the user selects the harmonic image, the controller 6 may control the image generation unit 7 such that the image generation unit 7 generates the harmonic image by using the first harmonic $2f_1$. Alternatively, if the user selects the second harmonic $3f_1$ during the process of generating the ultrasonic signal 4a, the controller 6 may provide a screen on the display unit 8 so that the user may select from a B-mode image and a harmonic image generated by using the second harmonic $3f_1$. If the user selects the harmonic image, the controller 6 may control the image generation unit 7 such that the image generation unit 7 generates the harmonic image by using the second harmonic $3f_1$.

Some example embodiments of ultrasonic diagnosis apparatuses for generating harmonic images and methods of generating ultrasonic images including the harmonic images have been described in detail with reference to the accompanying drawings.

It should be understood that the example embodiments described herein should be considered in a descriptive sense only and not for purposes of limitation. Descriptions of features or aspects within each embodiment should typically be considered as available for other similar features or aspects in other embodiments.

While some example embodiments of the present inventive concept have been described with reference to the figures, it will be understood by those of ordinary skill in the art that various changes in form and details may be made herein without departing from the spirit and scope of the present inventive concept as defined by the following claims.

What is claimed is:

1. An ultrasonic diagnosis apparatus, comprising:
an ultrasonic probe comprising an ultrasonic transducer configured to transmit an ultrasonic signal to an object and configured to receive an ultrasonic echo signal reflected from the object; and
one or more processors configured to,
control the ultrasonic probe such that the ultrasonic probe transmits the ultrasonic signal and receives the ultrasonic echo signal,
drive the ultrasonic transducer such that the ultrasonic signal simultaneously includes a fundamental frequency and at least one harmonic of the fundamental frequency, and
generate an ultrasonic image of the object based on the ultrasonic echo signal received by the ultrasonic probe,
wherein the one or more processors are further configured to generate the ultrasonic image of the object based on the at least one harmonic of the ultrasonic echo signal, the at least one harmonic of the ultrasonic echo signal being a sum of a first at least one harmonic component, which is generated by a nonlinear response from the object with respect to the fundamental frequency of the ultrasonic signal transmitted to the object, and a second at least one harmonic component, which is generated when the first harmonic of the ultrasonic signal transmitted to the object is reflected by linear response from the object.

2. The apparatus of claim 1, wherein the one or more processors are further configured to drive the ultrasonic transducer such that the ultrasonic signal transmitted to the object simultaneously includes the fundamental frequency and a first harmonic of the fundamental frequency.

3. The apparatus of claim 2, wherein the one or more processors are further configured to generate a harmonic image by using a first harmonic of the ultrasonic echo signal received by the ultrasonic probe.

4. The apparatus of claim 3, wherein the one or more processors are further configured to generate a B-mode image by using a fundamental frequency of the ultrasonic echo signal received from the ultrasonic probe.

5. The apparatus of claim 4, further comprising:
a display unit configured to display at least one of the harmonic image and the B mode image selected by the one or more processors.

6. The apparatus of claim 1, wherein the one or more processors are further configured to drive the ultrasonic transducer such that the ultrasonic signal transmitted to the object simultaneously includes the fundamental frequency and a second harmonic of the fundamental frequency.

7. The apparatus of claim 6, wherein the one or more processors are further configured to generate a harmonic image by using a second harmonic of the ultrasonic echo signal received by the ultrasonic probe.

8. The apparatus of claim 1, wherein the one or more processors further configured to drive the ultrasonic transducer such that the ultrasonic signal transmitted to the object simultaneously includes the fundamental frequency, a first harmonic of the fundamental frequency, and a second harmonic of the fundamental frequency.

9. The apparatus of claim 8, wherein the one or more processors are further configured to generate a B-mode image by using a fundamental frequency of the ultrasonic echo signal received from the ultrasonic probe, or generate a harmonic image by using at least one selected from a first harmonic and a second harmonic of the ultrasonic echo signal received from the ultrasonic probe.

10. The apparatus of claim 1, wherein the one or more processors are further configured to drive the ultrasonic transducer such that the ultrasonic signal transmitted to the object simultaneously includes the fundamental frequency and at least one selected from a first harmonic and a second harmonic of the fundamental frequency, depending on which is selected by a user.

11. A method of generating an ultrasonic image, the method comprising:
causing, by one or more processors, an ultrasonic transducer to transmit an ultrasonic signal to an object;
driving, by the one or more processors, the ultrasonic transducer such that the ultrasonic signal transmitted to the object simultaneously includes a fundamental frequency and at least one harmonic of the fundamental frequency;
causing, by the one or more processors, the ultrasonic transducer to receive an ultrasonic echo signal reflected from the object; and
generating, by the one or more processors, an ultrasonic image of the object based on the ultrasonic echo signal,
wherein the generating includes generating the ultrasonic image of the object based on the at least one harmonic of the ultrasonic echo signal that is a sum of a first at least one harmonic component, which is generated by a nonlinear response from the object with respect to the fundamental frequency of the ultrasonic signal transmitted to the object, and a second at least one harmonic component, which is generated when the first harmonic of the ultrasonic signal transmitted to the object is reflected by linear response from the object.

12. The method of claim 11, wherein the driving includes driving the ultrasonic transducer such that the ultrasonic signal transmitted to the object simultaneously includes the fundamental frequency and a first harmonic of the fundamental frequency.

13. The method of claim 12, wherein the generating includes generating a harmonic image by using a first harmonic of the ultrasonic echo signal.

14. The method of claim 13, wherein the generating further includes generating a B-mode image by using a fundamental frequency of the ultrasonic echo signal.

15. The method of claim 14, further comprising:
causing, by the one or more processors, at least one selected from the harmonic image and the B-mode image to be displayed on a display in response to a selection of a user.

16. The method of claim 11, wherein the driving includes driving the ultrasonic transducer such that the ultrasonic signal transmitted to the object simultaneously includes the fundamental frequency and a second harmonic of the fundamental frequency.

17. The method of claim 11, wherein the driving includes driving the ultrasonic transducer such that the ultrasonic signal transmitted to the object simultaneously includes the fundamental frequency, a first harmonic of the fundamental frequency, and a second harmonic of the fundamental frequency.

18. The method of claim 11, wherein the causing an ultrasonic transducer to transmit an ultrasonic signal to an object comprises:
selecting, by the one or more processors, at least one from the at least one harmonic of the fundamental frequency;

causing, by one or more processors, the ultrasonic transducer to generate the ultrasonic signal including the fundamental frequency and the selected at least one harmonic; and causing, by one or more processors, the ultrasonic transducer to transmit the generated ultrasonic signal to the object.

* * * * *